United States Patent [19]

Carter et al.

[11] Patent Number: 5,177,238

[45] Date of Patent: Jan. 5, 1993

[54] PREPARATION OF DIALKYL ALLYLPHOSPHONIC ACID DIESTERS

[75] Inventors: Charles G. Carter, Silver Spring, Md.; David R. Sterrenburg, Manitowoc, Wis.

[73] Assignee: W. R. Grace & Co. - Conn., New York, N.Y.

[21] Appl. No.: 730,752

[22] Filed: Jul. 16, 1991

[51] Int. Cl.$^5$ ............................................. C07F 9/40
[52] U.S. Cl. ..................................... 558/125; 558/217
[58] Field of Search .......................................... 558/125

[56] References Cited

U.S. PATENT DOCUMENTS

| | | | |
|---|---|---|---|
| 2,636,027 | 4/1953 | Coover et al. | 526/278 |
| 3,493,639 | 2/1970 | Tavs | 558/125 |
| 3,626,038 | 12/1971 | Steinberg | 558/87 |
| 3,830,890 | 8/1974 | Kerst et al. | 558/125 |
| 3,849,482 | 11/1974 | Christensen | 562/8 |
| 4,017,564 | 4/1977 | Arend et al. | 558/125 |
| 4,633,005 | 12/1986 | Nalewajek et al. | 558/125 |

FOREIGN PATENT DOCUMENTS 4875528 10/1973 Japan.
0512450 1/1976 Japan.

*Primary Examiner*—Mary C. Lee
*Assistant Examiner*—Michael G. Ambrose
*Attorney, Agent, or Firm*—Beverly K. Johnson

[57] ABSTRACT

An improved process for the production of allylphosphonic acid dialkyl esters in high yield and selectivity by the gradual addition of trialkyl phosphite to react with the appropriate allyl halide in the presence of a divalent nickel catalyst and, optionally, a polymerization inhibiting compound, e.g. hydroquinone.

17 Claims, No Drawings

PREPARATION OF DIALKYL ALLYLPHOSPHONIC ACID DIESTERS

FIELD OF THE INVENTION

The present invention relates to an improved process for the production of allylphosphonic acid dialkyl esters in high yield and selectivity by the gradual addition of trialkyl phosphite to react with the corresponding allyl halide in the presence of a divalent nickel catalyst and, optionally, a polymerization inhibiting compound.

BACKGROUND OF THE INVENTION

Allylphosphonic acid esters are useful intermediates to form compounds having a variety of applications. For example, allylphosphonic acid esters are useful as starting materials for the synthesis of medicinal products and agricultural chemicals. Allylphosphonic acid ester derivatives may also be converted into a fire-retardant polymer by copolymerizing with styrene, ethylene, vinyl chloride and the like.

Allylphosphonic acid esters are also useful intermediates to form allylphosphonic acids. Allylphosphonic acids have a variety of applications such as, for example, a starting material to prepare water-soluble polymers which have utility as water treatment additives.

Heretofore, allylphosphonic acid esters have been prepared by reaction of an allyl halide and trialkyl phosphite by either of three processes. The Michaelis-Arbusov reaction using allyl or methylallyl chloride was carried out in the absence of a catalyst under rigorous reaction conditions with moderate yields. It was not possible to obtain any reaction between allyl chloride and triethyl phosphite at normal pressure. Where the reaction was carried out under pressure, the yield obtained using a 10-molar excess of allyl chloride was at the most 53% according to A. E. Arbusov et al., Izvest. Akad. Nauk. SSSR, Otdel. Khigm, Nauk. 1951, 714.

In a second process according to Japan Kokai No. 73-75,528, the direct reaction of an allyl halide compound with a trialkyl phosphite compound was accomplished in the presence of a nickel halide catalyst at a high temperature. Another process involved heating an allyl halide compound and a trialkyl phosphite compound in the presence of an alkyl amine in a sealed tube. This process is described in detail in Compt. Rend 259:2244 (1964).

In the latter two processes, conversion of alkyl halide and trialkyl phosphite into the desired allylphosphonic acid ester is low and yields are not readily reproducible. The reaction product is generally a mixture of the allyl-phosphonate ester and the corresponding alkylphosphonate ester. The formation of the latter being the result of a side reaction which can drastically lower the yield of the desired allyl diester. The difficulty in separating the allyl ester and alkyl ester products may further threaten the yield of the desired allyl ester since the boiling points of the esters may be very close, such as, for instance, in the case of the allylphosphonic dimethyl ester and the methylphosphonic dimethyl ester.

U.S. Pat. No. 4,633,005 issued to David Nalewajek et al., discloses a process for preparing allylphosphonic esters in improved yields which process involves reacting an allyl halide with the appropriate phosphite in the presence of a phosphinated $d^8$-transition metal catalyst. This process is costly, however, since it requires the use of an expensive and complex phosphinated catalyst.

U.S Pat. No. 4,017,564 issued to Gunter Arend et al., discloses a process for the production of allylphosphonic acid esters by reacting allyl chloride with trialkyl phosphites at temperatures of from 80° to 160° C. in the presence of an avalent and/or monovalent nickel catalyst. The reference points out the inferiority of divalent nickel catalysts to produce allylphosphonate esters in good yield.

Accordingly, it is an object of the invention to provide a practical and efficient process for forming allylphosphonic acid esters in high selectivity and yield using a simple, inexpensive divalent nickel catalyst. It is also an object of this invention to provide an improved process for forming the allylphosphonate esters in the presence of a divalent nickel catalyst which process reduces formation of the alkylphosphonate esters, thereby forming an allyl ester product having increased purity.

Other objects will be evident from the ensuing description and appended claims.

SUMMARY OF THE INVENTION

The present invention is directed to a process which uses a combination of special parameters to unexpectedly provide a means of forming allylphosphonic acid ester in high conversion and selectivity by the reaction of trialkyl phosphite with allyl halide in the presence of a divalent nickel catalyst. The process permits the production of allylphosphonic acid esters having increased purity by minimizing the contact of the nickel catalyst with the starting trialkyl phosphite, thereby significantly decreasing the formation of unwanted side products.

The present process requires contacting under an inert atmosphere a mixture of a divalent nickel catalyst and, optionally, a polymerization-inhibiting compound with trialkyl phosphite and allyl halide. The trialkyl phosphite is introduced into the reaction zone gradually over substantially the entire time of the reaction. The allyl halide may be initially introduced or gradually introduced simultaneously with the trialkyl phosphite compound.

DETAILED DESCRIPTION

The present process is an improved process for forming allylphosphonic acid esters by the reaction of a trialkyl phosphite with an allyl halide in the presence of a divalent nickel catalyst and, optionally, a polymerization inhibitor. The process involves the gradual addition of the trialkyl phosphite over the course of the reaction. In general, the trialkyl phosphite should be added to the reaction at a rate such that the rate of addition of the trialkyl phosphite is substantially no greater than the maximum rate at which the trialkyl phosphite within the reaction zone is reacting with the allyl halide. That is, the appropriate trialkyl phosphite is added gradually at a rate such that the molar concentration of the trialkyl phosphite within the reaction vessel is equal to or less than the molar concentration of allyl halide. The trialkyl phosphite may be introduced neat when it is in liquid form or dissolved in an inert aromatic hydrocarbon (e.g. toluene or benzene) when it is in either a solid or a liquid form.

Typically, the rate of addition of the allyl halide is not critical, provided that the molar concentration of the allyl halide in the reaction zone is equal to or in excess of the trialkyl phosphite reactant. The allyl halide may be charged initially with the nickel catalyst and, if used, the polymerization inhibitor. Alternatively, depending upon the particular allyl halide used, the allyl halide may be introduced gradually into the reaction zone prior to or simultaneously with the appropriate trialkyl phosphite. For example, it is preferable to add allyl chloride simultaneously with the trialkyl phosphite reactant to avoid suppression of the temperature in the reaction vessel below the temperature at which the allyl halide reacts with the trialkyl phosphite reactant.

Trialkyl phosphite compounds which are useful as reactants the process of this invention are of the general formula

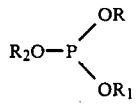

in which R, $R_1$ and $R_2$ are the same or different and are alkyl having from 1 to about 10 carbon atoms or cycloalkyl having from 3 to about 10 carbon atoms. Illustrative of permissible R, $R_1$ and $R_2$ substituents are alkyl such as methyl, ethyl, isopropyl, pentyl, sec-butyl, hexyl, isobutyl, heptyl and the like; cycloalkyl such as cyclobutyl, cyclopropyl, cyclohexyl, cyclopentyl and the like.

R, $R_1$ and $R_2$ substituents may be substituted with one or more functional groups which are relatively non-reactive with the reactants, product and catalyst employed in the process under the process conditions. Illustrative of such non-reactive functional groups are fluorine, alkylalkoxy (i.e. methylmethoxy, methylethoxy, methylpropoxy etc..) cyano, carboxy, alkoxycarbonyl, perfluoroalkyl (i.e. trifluoromethyl) and like non-reactive functional groups.

Preferred for use in the practice of this invention are phosphite compounds in which R, $R_1$ and $R_2$ are the same and are alkyl having from 1 to about 10 carbon atoms. Particularly preferred for use are compounds in which R, $R_1$ and $R_2$ are the same and are alkyl having from 1 to about 4 carbon atoms. Amongst these particularly preferred embodiments most preferred are those embodiments in which R, $R_1$ and $R_2$ are the same and are methyl or ethyl.

Phosphite compounds which can be used in the practice of this invention can be obtained from commercial sources or prepared in accordance with conventional procedures. For example, useful phosphite compounds can be conveniently prepared by reacting phosphorus trichloride with an appropriate alcohol as described in greater detail in "Organophosphorus Pesticides: Organic and Biological Chemistry" by Morhusa Eto, p. 19; CRC Press, Inc. (1979).

Allyl halide compounds which are useful as reactants in the process of this invention are of the formula:

wherein X is chlorine, bromine or iodine; $R_3$, $R_4$ and $R_5$ are the same or different and are hydrogen or alkyl. Preferred for use are such compounds in which X is chloro or bromo, and $R_3$, $R_4$ and $R_5$ are individually hydrogen, methyl or ethyl, and particularly preferred for use are such compounds in which X is chloro and $R_3$, $R_4$ and $R_5$ are hydrogen.

Useful allyl halides can be obtained from commercial sources or prepared in accordance with known preparative techniques. For example, allyl halide can be prepared by reacting corresponding olefin with a halogenating agent as for example elemental halogen at elevated temperature, or N-halosuccinimide in the presence of an initiator such as ultraviolet light or a peroxide. These reactions are as described in more detail in Horner et al., Agnew Chem 71:349-365 (1959); Boozer and Moncrief, J. Org. Chem., 27:623 (1962); and Waling and Thaler, J. Am. Chem. Soc., 83:3877 (1961).

The catalyst is a divalent nickel salt and is used in the present process in a "catalytically effective amount". As used herein, a "catalytically effective amount" is an amount of divalent nickel salt which is capable of catalyzing the reaction of the allyl halide and the phosphite reactant to any extent. Generally, the amount of catalyst used is from about 0.01 to 5.0 mole %, preferably from about 0.1 to 2.0 mole %, based on the amount of trialkyl phosphite used.

Suitable catalysts include nickel chloride, nickel bromide, nickel iodide, nickel nitrate, nickel carbonate, nickel sulfate, nickel cyanide, nickel thiocyanate, nickel acetyl acetonate, nickel acetate, nickel formate, nickel propionate, nickel butyrate and the like. Particularly preferred catalysts include nickel chloride, nickel bromide and nickel iodide.

It is generally known to add a polymerization inhibitor to increase the yield of the allyl ester. However, it was surprisingly found that the polymerization inhibitor also increased selectivity of the desired ester as well. Suitable polymerization inhibiting compounds for use in the present invention are, for example, hydroquinone, hydroquinone monomethyl ether, hydroquinone dimethyl ether, catechol, catechol monomethyl ether, 2,6-di-t-butyl-p-cresol and the like. Preferably, the polymerization inhibiting compound is hydroquinone. The polymerization inhibitor may be used in quantities of up to 5.0%, preferably up to about 2%, by weight based on the total weight of allyl halide.

The temperature employed in the process of this invention is critical and can be varied widely depending on factors known to those of skill in the art. Reaction will generally be carried out at a temperature greater than about 60° C. Temperatures within the range of from about 60° C. to about 150° C. are preferred and reaction temperatures of from about 80° C. to about 140° C. are particularly preferred. In the most preferred embodiments of the invention, the reaction is conducted at a temperature of from about 100° C. to about 130° C.

The reaction may be carried out at atmospheric and sub-atmospheric pressures in an open vessel. For convenience, the reaction is preferably carried out at atmospheric pressure.

The process of this invention is carried for a period of time sufficient to produce the desired compound in adequate yield. Reaction times are influenced to a significant degree by the reaction temperature; the concentration and choice of nickel catalyst; the concentration and choice of allyl and phosphite reactants; the choice and concentration of reaction solvent; and other factors known to those skilled in the art. In general, reaction times can vary from about a few minutes to 24 hours or longer.

The process of this invention can be conducted in a semicontinuous or continuous fashion. The reaction can be conducted in a single reaction zone or in a plurality of reaction zones, in series or in parallel, or it may be conducted intermittently or continuously in an elongated tubular zone or series of such zones. The materials of construction employed should be inert to the reactants during the reaction and the fabrication of the equipment should be able to withstand the reaction temperature and pressure.

The reaction can be carried out neat when one or both of the reactants and the product is a liquid under reaction conditions. A reaction solvent can be used when the reactants are either a liquid or a solid. Useful solvents include the allyl ester product itself, when it is a liquid, or other inert solvents such as aromatic hydrocarbons (i.e. toluene, benzene, high boiling ether solvents and the like). Preferred solvents include the allyl ester, toluene and benzene.

The allylphosphonic acid ester product can be isolated from the reaction mixture and purified using conventional techniques. Illustrative techniques include evaporation, distillation, solvent extraction and recrystallization. A variety of diester compounds can be prepared in accordance with the process of this invention by selecting appropriate starting materials and reaction conditions.

The process of the invention is further illustrated in the Examples below.

EXAMPLE I

Nickel chloride hexahydrate (pulverized, 1.189 g, 5.0 mmol) and 33 ml toluene were charged into a 250 ml flask under a nitrogen atmosphere. The catalyst was azeotropically dried by removal of 18 ml of toluene/water distillate. The distilling column was replaced with a reflux condenser and an addition funnel. Hydroquinone (1.106 g, 10.0 mmol) was added to the flask, and heating resumed. After reaching reflux, a small amount of trimethyl phosphite (1.27 g, 10.2 mmol) was added. This mixture was heated at reflux for 20 minutes with vigorous stirring. A mixture of trimethyl phosphite (124.8 g, 1.006 mole) and allyl chloride (88.12 g, 1.151 mole) was then added slowly over about 5 hours via the addition funnel. The rate of addition was controlled such that the reaction temperature was maintained at 100°–130° C. The reaction mixture was allowed to stir at 125° C. for an additional hour and analyzed by gas chromatograph (uncalibrated). This gas chromatograph analysis indicated incomplete conversion of the trimethyl phosphite. Another 10 ml (0.123 mmol) allyl chloride was added slowly over 1.5 hours while keeping the reaction temperature between 105° C. and 125° C. The reaction mixture was then allowed to stir at 115° C. for an additional ½ hour. Vacuum distillation of the product (90°–105° C./20mm) yielded 129.1 g of a clear liquid.

Quantitative proton NMR analysis of this product indicated the overall yields of dimethyl allylphosphonate and dimethyl methylphosphonate to be 76% and 2%, respectively, based on total trimethyl phosphite charged (selectivity 97/3).

EXAMPLE II

Nickel chloride hexahydrate (pulverized, 0.182 g., 0.77 mmol) and 10 ml toluene were charged into a flask under nitrogen atmosphere. The catalyst was azeotropically dried by distilling off about half of the solvent. The distilling column was replaced with a reflux condenser. Trimethyl phosphite (0.3 ml) was added to the slurry of the catalyst in toluene at 105° C. A mixture of allyl chloride (22.4 ml, 275 mmol) and trimethyl phosphite (31.27 g, 352 mmol) was added slowly via syringe pump over 12–15 hours. The rate of addition was adjusted so as to maintain the reaction temperature between 105° and 125° C. An additional portion of allyl chloride (2.0 ml, 25 mmol) was added over several hours while maintaining the reaction temperature between 100° C. and 110° C. Vacuum distillation of the product (100°–105° C./23 mmHg) yielded 28.5 g of a clear liquid.

Quantitative proton NMR analysis indicated the overall yields of dimethyl allylphosphonate and dimethyl methylphosphonate were 64% and 5.7%, respectively, based on the total trimethyl phosphite charged (selectivity 92/8).

COMPARATIVE EXAMPLE I

Allyl chloride (32.8 ml, 0.40 mole), trimethyl phosphite (48 ml, 0.40 mole) and anhydrous nickel (II) bromide (2.0 g., 0.009 mole) were charged into a flask under nitrogen atmosphere. The reaction mixture was heated to reflux for nine hours during which time the reflux temperature rose from 60° C. to 110° C. At this point, an additional 8.2 ml of allyl chloride (total 41.0 ml, 0.50 mole) was added over a period of two hours while maintaining the reaction at reflux. Distillation of the product under vacuum yielded 50.0 g. of a clear liquid.

Quantitative proton NMR analysis of the product indicated the overall yields of dimethyl allylphosphonate and dimethyl methylphosphonate to be 61% and 11%, respectively, based on trimethyl phosphite charged (Selectivity 85/15).

COMPARATIVE EXAMPLE II

Trimethyl phosphite (61.4 g., 495 mmol) was placed in a flask under nitrogen atmosphere together with a naphthalene internal standard (1.86 g.). Anhydrous nickel (II) bromide (0.56 g., 2.6 mmol) was added and the resulting mixture was heated to reflux. Over a period of 15 minutes, the color of the solution turned from dark red to pale yellow. At this point, 2.0 ml of allyl chloride was added. The remaining allyl chloride (45.0 ml total, 552 mmol) was added at a rate such that the reaction temperature was maintained between 100° C. and 125° C. Vacuum distillation of the product 44°–65° C./5mm) yielded 61.4 g. of a clear liquid.

Quantitative proton NMR analysis of the product indicated the overall yields of dimethyl allylphosphonate and dimethyl methylphosphonate to be 69% and 12%, respectively, based on trimethyl phosphite charged (selectivity 85/15).

We claim:

1. A process for the preparation of allylphosphonic acid dialkyl esters in improved yield and selectivity comprising reacting an allyl halide compound with a trialkyl phosphite compound in the presence of a catalytically effective amount of a divalent nickel catalyst and, optionally, a polymerization inhibiting compound, wherein the trialkyl phosphite compound is introduced into the reaction gradually over substantially the entire course of the reaction at a rate such that the molar concentration of the trialkyl phosphite is equal to or less than the molar concentration of allyl halide and the temperature is maintained within the range of about 60° C. to about 150° C.

2. The process of claim 1 wherein the temperature is maintained within the range of about 80° C. to about 140° C.

3. The process of claim 1 wherein the allyl halide compound is initially introduced into the reaction zone.

4. The process of claim 1 wherein the allyl halide compound is introduced into the reaction zone simultaneously with the trialkyl phosphite compound.

5. The process of claim 1 wherein the divalent nickel catalyst is selected from nickel chloride, nickel bromide, nickel iodide, nickel nitrate, nickel carbonate, nickel sulfate, nickel cyanide, nickel thiocyanate, nickel acetyl acetonate, nickel acetate, nickel formate, nickel propionate and nickel butyrate.

6. The process of claim 5 wherein the divalent nickel catalyst is nickel chloride, nickel bromide or nickel iodide.

7. The process of claim 1 wherein the amount of the catalyst is about 0.01 mole to about 5.0 mole percent based on the total moles of the trialkyl phosphite compound to be introduced.

8. The process of claim 1 wherein a polymerization inhibiting compound is added to the reaction vessel and is selected from hydroquinone, hydroquinone monomethyl ether, hydroquinone dimethyl ether, catechol, catechol monomethyl ether and 2,6-di-t-butyl-p-cresol.

9. The process of claim 8 wherein the polymerization inhibiting compound is hydroquinone.

10. The process of claim 8 wherein the polymerization inhibiting compound is present in the amount of up to 5% by weight of the allyl halide compound.

11. The process of claim 1 wherein the trialkyl phosphite compound is a liquid under the reaction conditions and is introduced into the reaction neat.

12. The process of claim 1 wherein the trialkyl phosphite compound is a solid and is introduced into the reaction zone dissolved in a non-reactive solvent.

13. The process of claim 1 wherein allyl halide compound is reacted with a trialkyl phosphite compound of the general formula

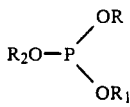

in which R, $R_1$ and $R_2$ are, independently, alkyl having from 1 to 10 carbon atoms or cycloalkyl having from 3 to 10 carbon atoms.

14. The process of claim 13 wherein the trialkyl phosphite compound is reacted with an allyl halide compound of the formula $$R_3R_4C=CR_5-CH_2X$$

in which X is chlorine, bromine or iodine; and $R_3$, $R_4$ and $R_5$ are, independently, hydrogen or alkyl.

15. The process of claim 14 wherein an allyl halide compound in which X is chlorine and each of $R_3$, $R_4$ and $R_5$ is hydrogen, is reacted with a trialkyl phosphite compound wherein R, $R_1$ and $R_2$ are the same and are alkyl having from 1 to 4 carbon atoms.

16. The process of claim 15 wherein allyl chloride is reacted with a trialkyl phosphite in which each of R, $R_1$ and $R_2$ are methyl.

17. The process of claim 15 wherein allyl chloride is reacted with a trialkyl phosphite in which each of R, $R_1$ and $R_2$ are ethyl.

* * * * *